United States Patent
Sullivan

(10) Patent No.: US 9,566,279 B1
(45) Date of Patent: *Feb. 14, 2017

(54) HEMATOLOGICAL TREATMENTS BASED ON LEVOMEFOLATE

(71) Applicant: Cox Bioscience LLC, New York, NY (US)

(72) Inventor: Clark Gerald Sullivan, New York, NY (US)

(*) Notice: Subject to any disclaimer, the term of this patent is extended or adjusted under 35 U.S.C. 154(b) by 99 days.

This patent is subject to a terminal disclaimer.

(21) Appl. No.: 14/226,661

(22) Filed: Mar. 26, 2014

Related U.S. Application Data

(60) Provisional application No. 61/805,184, filed on Mar. 26, 2013, provisional application No. 61/805,181, filed on Mar. 26, 2013.

(51) Int. Cl.
| | | |
|---|---|---|
| *A61K 31/519* | (2006.01) | |
| *A61K 31/714* | (2006.01) | |
| *A61K 33/26* | (2006.01) | |
| *A61K 45/06* | (2006.01) | |

(52) U.S. Cl.
CPC ........... *A61K 31/519* (2013.01); *A61K 31/714* (2013.01); *A61K 33/26* (2013.01); *A61K 45/06* (2013.01)

(58) Field of Classification Search
None
See application file for complete search history.

(56) References Cited

PUBLICATIONS

Bart et al., "Folate status and homocysteine levels during a 24-week oral administration of a folate-containing oral contraceptive: a randomized, double-blind, active-controlled, parallel-group, US-based multicenter study", Contraception 85 (2012) pp. 42-50.*
Whittle, et al. Folate supplementation and methotrexate treatment in rheumatoid arthritis: a review; Rheumatology 2004;43:267-271.
Mueller et al. Interrelationship of Folic Acid, Vitamin B12 and Ascorbic Acid in Patients with Megaloblastic Anemia; The American Journal of Clinical Nutrition, vol. 3, No. 1: pp. 30-44; 1955.
Saraya, et al. Intestinal structure and function in megaloblastic anemia in adults; Am J Clin Nutr 24:1971, pp. 622-627.
Vilter, et al. Studies on the Relationships of Vitamin B12, Folic Acid, Thymine, Uracil, and Methyl Group Donors in Persons With Pernicious Anemia and Related Megaloblastic Anemias; Blood the Journal of Hematology, vol. V, No. 8, 1950 pp. 695-717.
Haurani, el al. Megaloblastic Anemia Probably Caused by Defective Utilization of Folinic Acid; Blood the Journal of Hematology 1960, 16:1546-1554.
Sheehy, et al. The Effect of "Minute" and "Titrated" Amounts of Folic Acid on the Megaloblastic Anemia of Tropical Sprue; Blood the Journal of Hematology 1961, 18:623-636.
Taheri, et al. The effect of folate analogues and vitamin B12 on provision of thymine nucleotides for DNA synthesis in megaloblastic anemia; Blood the Journal of Hematology 1982, 59: 634-640.
Carmel, et al. The Laboratory Diagnosis of Megaloblastic Anemias; West J Med 128:294-304, Apr. 1978.
Dhir, et al. Comparison of two different folic acid doses with methotrexate—a randomized controlled trial (FOLVARI Study); Arthritis Research & Therapy (2015) 17:156, pp. 1-9.
Ralph Green; Indicators for assessing folate and vitamin B12 status and for monitoring the efficacy of intervention strategies; Food and Nutrition Bulletin, vol. 29, No. 2; 2008, The United Nations University.
Blackwell Science Ltd. Historical Review: The HIstory of Folic Acid; The British Journal of Haematology 2001, 113: 579-589.
Lindenbaum; Status of laboratory testing in the diagnosis of megaloblastic anemia; Blood, 1983 vol. 61, No. 4: 324-627.
Morgan, et al. Supplementation with Folic Acid during Methotrexate Therapy for Rheumatoid Arthritis; Ann Intern Med. 1994; 121:833-841.
Morgan, et al. Folate supplementation during methotrexate therapy for rheumatoid arthritis; Clin. Exp Rheumatol 2010; 28 (supple. 61): S102-S109.
Pentieva; et al. The short-term bioavailabilities of [6S1]-5-Methyltetrahydrofolate and folic acid are equivalent in men; J Nutr, 134:580-585; 2004.
Pietrzik; et al. Folic Acid and L-5-Methyltetrahydrofolate; Clin Pharmacoklnet 2010; 49(8): 535-548.
Prinz-Langenohl; et al. 169-Poster and Pentieva; et al. 170-Poster; J. Inherit. Metab. Dis. 26 (2003) Suppl. 1.
Robinson et al. Lack of Clinical Utility of Folate Levels in the Evaluation of Macrocytosis or Anemia; Am J Med. 2001;110:88-90.
Selhub, et al. The use of blood concentrations of vitamins and their respective functional indicators to define folate and vitamin B12 status; Food and Nutrition Bulletin, vol. 29, No. 2 (supplement) 2008.
Song, et al. Association of the MTHFR C677T and A1298C polymorphisms with methotrexate toxicity in rheumatoid arthritis: a meta-analysis; Clin Rheumatol (2014) 33:1715-1724.
van Ede, et al. Effect of Folic or Folinic Acid Supplementation on the Toxicity and Efficacy of Methotrexate in Rheumatoid Arthritis; Arthritis & Rheumatism; vol. 44, No. 7, Jul. 2001, pp. 1515-1524.
van Ede; et al. Homocysteine and folate status in methotrexate-treated patients with rheumatoid arthritis; Rheumatology 2002;41:658-665.

* cited by examiner

*Primary Examiner* — Carlos Azpuru
*Assistant Examiner* — Casey Hagopian
(74) *Attorney, Agent, or Firm* — Clark G Sullivan

(57) ABSTRACT

Methods of treating hematological disorders including macrocytosis, and for decreasing hematological markers such as mean corpuscular volume, homocysteine and methylmalonic acid are described, based on the administration of levomefolate, optionally in combination with vitamin B12, iron or an anti-folate drug.

19 Claims, No Drawings

HEMATOLOGICAL TREATMENTS BASED ON LEVOMEFOLATE

RELATED APPLICATIONS

The present application claims priority to provisional U.S. Application No. 61/805,184, filed Mar. 26, 2013, and 61/805,181, filed Mar. 26, 2013.

FIELD OF THE INVENTION

This invention relates to pharmaceutical therapies, particularly to hematological treatments based upon therapeutically effective combinations of cobalamin plus levomefolate or its pharmaceutically acceptable salts.

BACKGROUND

Levomefolate, also known as L-5-methyltetrahydrofolate or "LMF", is a naturally occurring compound essential to folate metabolism. Its calcium salt has the below chemical structure:

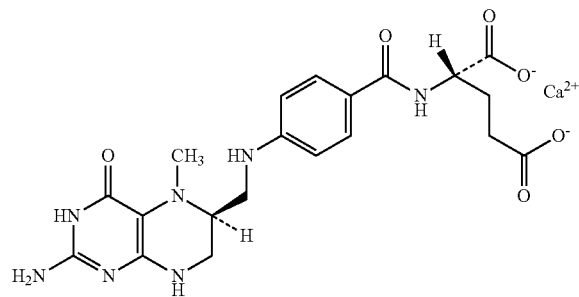 [SMILES: CN1c2c(nc(N)[nH]c2=O)NC[C@@H]1CNc1ccc(C(=O)N[C@@H](CCC(=O)[O-])C(=O)[O-])cc1 ; [Ca+2]]

The molecule can exist as a glutamated or non-glutamated form.

As can be seen, the molecule has a fully reduced pyrazine ring, a methyl constituent at the N5 position, and a single glutamate residue. It is approved by the Food and Drug Administration for the prevention of neural tube defects in two marketed birth control pills (Beyaz® and Safyral®). It has also been shown to decrease homocysteine levels in apparently healthy human subjects.

The molecule has not, however, found widespread medical use because of its inherent instability, and the lack of studies on its metabolism and molecular pharmacology. What is needed are studies to determine its efficacy in disease states and in a normal functioning metabolism, and methods that take advantage of such studies.

SUMMARY OF THE INVENTION

Novel therapies against depressed hemoglobin levels, elevated MCV, and abnormal levels of other markers of hematological health such as red cell count, reticulocyte count, and LDH, have been developed based on the discovery that increasing levomefolate concentrations without interference by unmetabolized folic acid has a consistently positive impact on these markers, but that increasing folate status in the presence of unmetabolized folic acid has a negative impact on these markers. This is true in the general population tested, as well as patients with healthy vitamin B12 levels or healthy iron levels. The methods have particular applicability in the treatment of folate deficient megaloblastic anemia, characterized by megaloblasts in the bone marrow and hypersegmented neutrophils in the peripheral blood cells, among other criteria.

Based on these discoveries, the inventors have developed methods for improving the hematological status of patients that relies on the administration of levomefolate, optionally by co-administering vitamin B12 or iron. Therefore, in a first principal embodiment the invention provides a method of modulating a hematological marker in a human subject in need thereof comprising administering to said subject a therapeutically effective amount of levomefolate or a pharmaceutically acceptable salt thereof, optionally in combination with a second therapeutic agent selected from vitamin B12 and iron, wherein said method of modulating a hematological marker is selected from the group consisting of: (a) increasing serum hemoglobin levels; (b) lowering serum lactate dehydrogenase levels; (c) lowering serum C-reactive protein levels; (d) lowering mean corpuscular volume levels; (e) increasing red cell count levels; (f) lowering serum homocysteine levels; (g) lowering serum methylmalonic acid levels; and (h) increasing reticulocyte levels.

In a second principal embodiment the invention provides a method of treating a hematological disorder in a human subject in need thereof comprising administering to said human a therapeutically effective amount of levomefolate or a pharmaceutically acceptable salt thereof, optionally in combination with a second therapeutic agent selected from vitamin B12 and iron, wherein said hematological disorder is selected from the group consisting of: (a) depressed serum hemoglobin levels; (b) elevated serum lactate dehydrogenase levels; (c) elevated serum C-reactive protein levels; (d) elevated mean corpuscular volume levels; (e) depressed red cell count levels; (f) elevated homocysteine levels; (g) elevated methylmalonic acid levels; and (h) depressed reticulocyte levels.

In yet another principal embodiment the invention provides a method of treating a hematological disorder in a human subject in need thereof comprising administering to said subject a therapeutically effective amount of levomefolate or a pharmaceutically acceptable salt thereof, optionally in combination with a second therapeutic agent selected from vitamin B12 and iron, wherein said hematological disorder is selected from the group consisting of: (a) anemia; (b) macrocytosis; (c) macrocytic anemia; (d) impaired folate metabolism due to anti-folate therapy; and (e) megaloblastic anemia.

Still other embodiments relate to the unique dosage forms of the present invention and in one embodiment the invention provides a solid oral dosage form comprising one or more pharmaceutically acceptable excipients, from 0.4 to 1.0 mg of levomefolate or a pharmaceutically acceptable salt thereof, and from 25 to 1000 mcg of vitamin B12. In another embodiment the invention provides a solid oral dosage form comprising one or more pharmaceutically acceptable excipients, from 0.333 to 1.0 mg of levomefolate or a pharmaceutically acceptable salt thereof, and from 67 to 400 mg of iron.

Additional advantages of the invention are set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

Definition and Use of Terms

When the singular forms "a," "an" and "the" or like terms are used herein, they will be understood to include plural referents unless the context clearly dictates otherwise. Thus, for example, reference to "a hydrocarbon" includes mixtures of two or more such hydrocarbons, and the like. The word "or" or like terms as used herein means any one member of a particular list and also includes any combination of members of that list.

When used herein the term "about" or "ca." will compensate for variability allowed for in the pharmaceutical industry and inherent in pharmaceutical products, such as differences in product strength and bioavailability due to manufacturing variations and time-induced product degradation. The term allows for any variation which in the practice of pharmaceuticals would allow the product being evaluated to be considered pharmaceutically equivalent or bioequivalent, or both if the context requires, to the recited strength of a claimed product. It will be understood that all numeric values expressed in this document can be prefaced by the term "about."

Throughout the description and claims, when a vitamin or mineral is "administered," it will be understood that the vitamin or mineral can be consumed or otherwise ingested as part of the subject's normal food diet. When a vitamin or mineral is administered as a supplement, it will be understood that the vitamin or mineral is not administered as part of the subject's normal diet, but is instead administered in a supplemental dosage form such as a capsule, pill or tablet.

The term "apparently healthy" or "apparently normal" means that, while the subject appears healthy based on vitamin levels within the normal range established by NHANES, the subject's vitamin levels are actually inducing or supporting hematological abnormalities that would be reversed upon administration of a therapeutically effective amount of the vitamin.

Throughout the description and claims of this specification, the word "comprise" and variations of the word, such as "comprising" and "comprises," means "including but not limited to," and is not intended to exclude, for example, other additives, components, integers or steps.

When a range of values can be used to describe a particular regimen, it will be understood that the range can be defined by selectively combining any one of the lower end of variables described in the specification with any one of the upper end of variables described in the specification that is mathematically possible.

The terms "treating" and "treatment," when used herein, refer to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, the term "significantly" refers to a level of statistical significance. The level of statistical significant can be, for example, of at least $p<0.05$, of at least $p<0.01$, of at least $p<0.005$, or of at least $p<0.001$. Unless otherwise specified, the level of statistical significance when recited is $p<0.05$. When a measurable result or effect is expressed or identified herein, it will be understood that the result or effect is preferably evaluated based upon its statistical significance relative to a baseline. In like manner, when a treatment is described herein, it will be understood that the treatment preferably shows efficacy to a degree of statistical significance.

As used herein, "therapeutically effective amount" refers to an amount sufficient to elicit the desired biological response. The therapeutically effective amount or dose will depend on the age, sex and weight of the patient, and the current medical condition of the patient. The skilled artisan will be able to determine appropriate dosages depending on these and other factors in addition to the present disclosure. By definition, an amount of a vitamin or mineral adequate to correct or maintain basal levels of the vitamin or mineral above a depressed or deficient state are therapeutically effective. The 2013 dietary reference intakes for folates (400 mcg/day) based on dietary folate equivalents ("DFEs"), the dietary reference intakes for vitamin B12 (2.4 mcg/day), the dietary reference intakes for iron (27 mg/day for pregnant women), and any larger amount up to the maximum level of daily nutrient intake that is likely to pose no risk of adverse effects, are therapeutically effective for practicing the methods of the present invention. The DRI are also known as recommended dietary allowances ("RDA"), and are published by Food and Nutrition Board of the Institute of Medicine, National Academy of Sciences.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use. "Pharmaceutically acceptable salts" means salts that are pharmaceutically acceptable, as defined above, and which possess the desired pharmacological activity.

When a weight of an active ingredient is given without reference to the free base or salt of the active ingredient, it will be understood that the weight can refer to the weight of the free base of the weight or the entire salt. Thus, for example, a method that can be practiced with 1.0 mg levomefolate can be practiced with 1.0 mg of levomefolate calcium based on the weight of the free base or 1.0 mg based on the weight of the entire salt. In like manner, when a weight of a mineral that exists in several forms is given, it will be understood that the weight can refer to the total weight of the mineral in the particular form at issue, or just the elemental portion of the mineral. Thus, for example, a method that can be practiced with 0.4 mg of iron can be practiced with 0.4 mg of iron sulfate or chelated iron based on the weight of the elemental iron in the compound or chelate, or based on the weight of the entire molecule including the sulfate or the chelate.

"Cobalamin" refers to α-(5,6-dimethylbenzimidazolyl) cobamide having an axial R-group bound to the cobalt atom, as illustrated by the following structure:

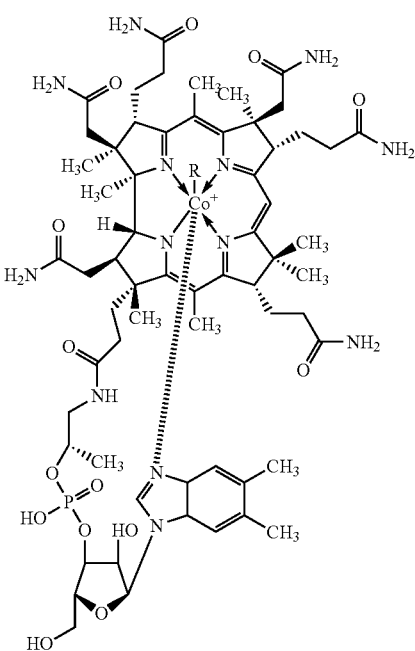

Cobalamins with which the invention can be practiced include cyanocobalamin, hydroxocobalamin, methylcobalamin, and adenosylcobalamin. As used herein, the term "vitamin B12" will be used synonymously with cobalamin, and will include all active forms of cobalamin. When a weight quantity of cobalamin or vitamin B12 is given herein, it will be understood to refer to the weight quantity of the particular cobalamin species under consideration, including the R-group, regardless of which R-group is appended.

"Iron" refers to any form of iron that is generally recognized as safe among experts qualified in iron supplementation, and includes carbonyl iron, iron sulfate, polysaccharide iron complexes (e.g. zinc gluconate), and chelated irons (e.g. zinc bisglycinate).

"Macrocytosis" refers to a condition involving the abnormal enlargement of red blood cells, and is typically defined in terms of mean corpuscular volume. In various embodiments, macrocytosis is defined based on a mean corpuscular volume exceeding 95, 98, 99, 100, 105, or even 110 femtoliters (fL).

"Mean corpuscular volume" or "MCV" is a measure of the average red blood cell size that is typically reported as part of a standard complete blood count. The MCV is calculated by dividing the total volume of packed red blood cells (also known as hematocrit) by the total number of red blood cells. Elevated MCV refers to a mean corpuscular volume exceeding 95, 98, 99, 100, 105, or even 110 femtoliters (fL).

Methylmalonic acid or "MMA" is a dicarboxylic acid that is a C-methylated derivative of malonate. The coenzyme A linked form of methylmalonic acid, methylmalonyl-CoA, is converted into succinyl-CoA by methylmalonyl-CoA mutase, in a reaction that requires vitamin B12 as a cofactor. In this way, it enters the Krebs cycle, and is thus part of one of the anaplerotic reactions. An "elevated MMA level" refers to a serum MMA level exceeding 180 nmol/L, 210 nmol/L, 240 nmol/L, 270 nmol/L, or 300 nmol/L.

"Homocysteine" or "HCY" is a protein amino acid. It is a homologue of the amino acid cysteine, differing by an additional methylene bridge (—CH2-). It is biosynthesized from methionine by the removal of its terminal methyl group. Homocysteine can be recycled into methionine or converted into cysteine with the aid of B-vitamins. An "elevated HCY level" refers to a serum HCY level exceeding 13 umol/L, 15 umol/L, 16 umol/L, 17 umol/L, or 19 umol/L.

"Vitamin B12 deficiency" is any deficiency of cobalamin leading to subtle or overt hematological or neurological changes in a human subject. Vitamin B12 deficiency can be defined as serum vitamin B-12<148 pmol/L or serum MMA ≥210 nmol/L, which are above the published reference range for serum vitamin B-12-replete individuals with normal serum creatinine concentrations in Pfeiffer et al., Am J. Clin. Nutr. 2005; 82:442-50. In like manner, a patient having a "normal" level of vitamin B12 will preferably have a serum vitamin B12 level ≥148 pmol/L. Vitamin B12 deficiency can also be defined based on other serum levels of vitamin B12, including any concentration less than 160, 190, 221, or 250 pmol/L.

Biomarker test assays—unless otherwise indicated herein, all biomarker test assays are performed in accordance with standard procedures employed during the 2001-2002 cycle of the National Health and Nutrition Examination Survey.

When used herein to describe levels of markers in a human subject, the terms "depressed" or "deficiency" mean that the marker under consideration is present at levels below typically considered normal by reference laboratories. In like manner, an "elevated" level of a marker means that the marker under consideration is present at levels above those typically considered normal by reference laboratories. It will be understood that normal ranges vary from laboratory to laboratory, and that they preferably refer to normal reference ranges established by the National Health and Nutrition Examination Survey.

Discussion

As mentioned above, the inventors have developed methods for improving the hematological status of patients that relies on the administration of levomefolate, optionally in combination with other vitamins, minerals, or traditional pharmacological agents. In a first principal embodiment the invention provides a method of modulating a hematological marker in a human subject in need thereof comprising administering to said human a therapeutically effective amount of levomefolate or a pharmaceutically acceptable salt thereof, wherein said method of modulating a hematological marker is selected from the group consisting of: (a) increasing serum hemoglobin levels; (b) lowering serum lactate dehydrogenase levels; (c) lowering serum C-reactive protein levels; (d) lowering mean corpuscular volume levels; (e) increasing red cell count levels; (f) lowering serum homocysteine; (g) lowering serum methylmalonic acid; and (h) increasing reticulocyte levels.

In a second principal embodiment the invention provides a method of treating a hematological disorder in a human subject in need thereof comprising administering to said human a therapeutically effective amount of levomefolate or a pharmaceutically acceptable salt thereof, wherein said hematological disorder is selected from the group consisting of: (a) depressed serum hemoglobin levels; (b) elevated serum lactate dehydrogenase levels; (c) elevated serum C-reactive protein levels; (d) elevated mean corpuscular volume levels; (e) depressed red cell count levels; (f) elevated serum homocysteine; (g) elevated serum methylmalonic acid; and (h) depressed reticulocyte levels.

In a third principal embodiment the invention provides a method of treating a hematological disorder in a human subject in need thereof comprising administering to said human a therapeutically effective amount of levomefolate or a pharmaceutically acceptable salt thereof, wherein said hematological disorder is selected from the group consisting of: (a) anemia; (b) macrocytosis; (c) macrocytic anemia; (d) impaired folate metabolism due to anti-folate therapy; and (e) megaloblastic anemia.

In any of the foregoing principal embodiments, the subject in need of modulating a hematological marker or treating a hematological disorder can be defined based on one or any combination of the following principal criteria:

depressed serum hemoglobin levels, i.e. serum hemoglobin levels less than 14.5, 14.0, 13.8, 13.5, 13.0, 12.5, 12.1, 12.0, 11.8, 11.5, 11.0, 10.5 or 10.0 g/dL (preferably less than 13.8 g/dL for men and 12.1 g/dL for women, respectively);

elevated serum lactate dehydrogenase ("LDH") levels, i.e. serum LDH levels greater than 90, 120, 150, 180, 198, 220, 250, 280, or 333 IU/L (preferably greater than 198 IU/L);

elevated serum C-reactive protein ("CRP") levels, i.e. serum CRP levels greater than 180, 200, 220, 240, or 260 nmol/L (preferably 200 or 240 nmol/L);

elevated mean corpuscular volume ("MCV") levels, i.e. MCV levels greater than 94, 95, 98, 99, 100, 105, 110 or 115 fL (preferably greater than 100 fL);

depressed red cell count ("RCC") levels, i.e. RCC levels less than 5.2, 4.7, 4.2 or 4.0 million/uL (million red cells per microliter of blood) (preferably less than 4.7 million/uL for men and 4.2 million/uL for women);

depressed reticulocyte levels, i.e. reticulocyte levels less than 0.8%, 0.7%, 0.6%, 0.5%, 0.4% or 0.3% (as a percentage of red blood cells) (preferably less than 0.5%);

elevated homocysteine levels, i.e. serum homocysteine levels greater than 14.0, 15.0, 16.0, or 17.0 umol/L (preferably greater than 16 umol/L);

depressed serum folate levels; i.e. serum folate levels less than 5.0, 4.0, 3.5, 3.0, 2.5 or 2.0 ng/mL (preferably less than 3.0 ng/mL);

depressed RBC folate levels, i.e. RBC folate levels less than 200, 175, 151, 150, 140, or 125 ng/mL (preferably less than 151 ng/mL);

diagnosed anemia or anemia, i.e. depressed hemoglobin (preferably <13.8 or 12.1 g/dL for men and women, respectively);

diagnosed macrocytosis or macrocytosis, i.e. elevated MCV (preferably >100 fL);

diagnosed macrocytic anemia or macrocytic anemia, i.e. depressed hemoglobin (preferably <13.8 or 12.1 g/dL for men and women, respectively) and elevated MCV (preferably >100 fL);

diagnosed megaloblastic anemia or megaloblastic anemia, i.e. blood cell morphology characterized by hypersegmented neutrophils (neutrophil white blood cells containing more than the average normal of 3 lobes in their nuclei), bone marrow pathology consistent with megaloblastic anemia (i.e. many large immature and dysfunctional red blood cells (megaloblasts) in the bone marrow, and elevated MCV (preferably >100 fL); and/or impaired folate metabolism due to anti-folate therapy, including methotrexate, pemetrexed, proquanil, pyrimethamine, trimethoprim, trimetrexate, edatrexate, piritrexim, and lometrexol.

It will be understood that normal levels of the foregoing principal criteria will differ depending on the age, sex, and health status of the individual being evaluated, and that all of the foregoing values can be selected and applied to males and females independently, particularly hemoglobin levels and red cell count levels.

When defining whether a subject is in need of modulating a hematological marker or treating a hematological disorder, consideration should also be given to whether the subject is deficient in vitamin B12 or iron. Thus, a subject is in need of modulating a hematological marker or treating a hematological disorder if, in addition to satisfying any of cut points for the foregoing principal criteria, the patient meets one or a combination of the following secondary criteria:

depressed vitamin B12 levels, i.e. serum B12 less than 400, 300, 250, 220, 200, or 180 pg/mL, preferably less than 200 pg/mL;

elevated serum methylmalonic acid ("MMA") levels, i.e. serum MMA greater than 180, 200, 210, 220, 240 or 250 nmol/L, preferably greater than 210 nmol/L, and/or depressed serum iron levels, i.e. serum iron levels less than 50, 55, 60, 65, 70 or 75 mcg/dL, preferably less than 60 mcg/mL;

Alternatively, in addition to satisfying any of the cut points for the foregoing principal criteria, the patient might meet one or a combination of the following secondary criteria:

normal vitamin B12 levels, i.e. serum B12 levels greater than 180, 200, 250, 300 or 400 pg/mL, preferably greater than 200 pg/mL, normal serum MMA levels, i.e. serum MMA less than 250, 240, 220, 210, 200, or 180 nmol/L, preferably less than 210 nmol/L, and/or normal serum iron levels, i.e. serum iron greater than 50, 55, 60, 65, 70 or 75 mcg/dL, preferably greater than 60 mcg/mL;

Preferred principal sets of principal and secondary criteria for determining whether the subject is in need of modulating a hematological marker or treating a hematological disorder include:

elevated MCV (preferably greater than 100 fL) and depressed serum folates (preferably less than 3 ng/mL);

elevated MCV (preferably greater than 100 fL), depressed serum folates (preferably less than 3 ng/mL), and depressed RBC folates (preferably less than 151 ng/mL);

elevated MCV (preferably greater than 100 fL), depressed serum folates (preferably less than 3 ng/mL), depressed RBC folates (preferably less than 151 ng/mL), and normal vitamin B12 levels (preferably greater than 200 pg/mL);

elevated MCV (preferably greater than 100 fL), depressed serum folates (preferably less than 3 ng/mL), depressed RBC folates (preferably less than 151 ng/mL), normal vitamin B12 levels (preferably greater than 200 pg/mL), and elevated LDH (preferably greater than 198 IU/L);

elevated MCV (preferably greater than 100 fL), depressed serum folates (preferably less than 3 ng/mL), depressed RBC folates (preferably less than 151 ng/mL), normal vitamin B12 levels (preferably greater than 200 pg/mL), and elevated HCY (preferably greater than 16 umol/L);

elevated MCV (preferably greater than 100 fL), depressed serum folates (preferably less than 3 ng/mL), depressed RBC folates (preferably less than 151 ng/mL), normal vitamin B12 levels (preferably greater than 200 pg/mL), elevated LDH (preferably greater than 198 IU/L), and elevated HCY (preferably greater than 16 umol/L);

diagnosed megaloblastic anemia and depressed serum folates (preferably less than 3 ng/mL);

diagnosed megaloblastic anemia, depressed serum folates (preferably less than 3 ng/mL), and depressed RBC folates (preferably less than 151 ng/mL);

diagnosed megaloblastic anemia, depressed serum folates (preferably less than 3 ng/mL), depressed RBC folates (preferably less than 151 ng/mL), and normal vitamin B12 levels (preferably greater than 200 pg/mL);

diagnosed megaloblastic anemia, depressed serum folates (preferably less than 3 ng/mL), depressed RBC folates (preferably less than 151 ng/mL), normal vitamin B12 levels (preferably greater than 200 pg/mL), and elevated LDH (preferably greater than 198 IU/L);

diagnosed megaloblastic anemia, depressed serum folates (preferably less than 3 ng/mL), depressed RBC folates (preferably less than 151 ng/mL), normal vitamin B12 levels (preferably greater than 200 pg/mL), and elevated HCY (preferably greater than 16 umol/L); and diagnosed megaloblastic anemia, depressed serum folates (preferably less than 3 ng/mL), depressed RBC folates (preferably less than 151 ng/mL), normal vitamin B12 levels (preferably greater than 200 pg/mL), elevated LDH (preferably greater than 198 IU/L), and elevated HCY (preferably greater than 16 umol/L).

Preferred secondary sets of criteria for determining whether the subject is in need of treatment according to any of the principal embodiments include any of the primary sets of criteria in combination with:

an above normal methylmalonic acid level (preferably less than 210 nmol/mL);

a below normal level of serum hemoglobin (preferably less than 13.8 g/dL for men and 12.1 g/dL for women, respectively);

an above normal level of C-reactive protein (preferably greater than 200 or 240 nmol/L);

a below normal red cell count (preferably less than 4.7 million/uL for men and 4.2 million/uL for women); and/or a below normal reticulocyte count (preferably less than 0.5% as a percentage of red blood cells).

A therapeutically effective amount of levomefolate for purposes of any of the principal embodiments, regardless of the criteria used to determine the subject's need for the treatment, of this invention can range from 0.3, 0.4, 0.5, 0.6, 0.7, 0.8, 0.9, or 1.0 mg/day, up to 25, 20, 15, 10, 5, 2.5, 2.0, 1.5, or 1.2 mg/day. The dose can be administered once as a single dose, or divided into two, three or four doses. The dose can be administered as the free base or as a pharmaceutically acceptable salt. In a preferred embodiment, from 0.4 to 1.0 mg of levomefolate is administered, preferably as the calcium salt. In an even more preferred embodiment, 0.4, 0.5, or 1.0 mg/day of levomefolate is administered, preferably as the calcium salt. This dose can be based on the weight of the free base or the entire salt.

In any of the foregoing embodiments, the administration of levomefolate can be combined with vitamin B12 and/or iron, preferably in a therapeutically effective amount. When orally administered, the amount of B12 administered will depend whether an an intestinal absorption problem is suspected in the subject. If there are no absorption issues, a therapeutically effective amount of vitamin B12 can range from 1.5 mcg to 50 mcg, from 1.5 to 5 mcg/day, from 2.0 to 3.5 mcg/day, from 2.2 to 3.0 mcg/day, from 15 to 50 mcg/day, from 20 to 35 mcg/day, or 25 mcg/day. If absorption issues are suspected, a therapeutically effective amount of vitamin B12 can range from 500, 600, 700, 800 or 900 mcg to 5,000, 4,000, 3,000, 2,000, or 1,500 mcg of vitamin B12 per day, preferably from 500 to 1,500 mcg, or from 800 to 1,200 mcg, and most preferably 1,000 mcg per day.

As with the levomefolate, any of these vitamin B12 doses can be administered once as a single dose, or divided into two, three or four doses. In one embodiment the levomefolate and vitamin B12 are provided in a unitary oral dose, such as a tablet or capsule. In this embodiment the invention provides a solid oral dosage form comprising one or more pharmaceutically acceptable excipients, from 0.4 to 1.0 mg of levomefolate or a pharmaceutically acceptable salt thereof, and from 25 to 1000 mcg of vitamin B12. Alternatively, the invention provides an oral dosage form comprising 0.4, 0.5, or 1.0 mg of levomefolate (preferably as levomefolate calcium) and 2.5, 3.5, 25, 100, 250, 500, 750, 1,000, 1,250 or 1,500 mcg of vitamin B12 (preferably as cyanocobalamin).

The combination of levomefolate and vitamin B12 has proven especially useful in the supportive care setting when protecting against the adverse effects of anti-folate drugs. Anti-folates with which the methods of the present invention can be practiced include, for example, methotrexate, pemetrexed, proquanil, pyrimethamine, trimethoprim, trimetrexate, edatrexate, piritrexim, and lometrexol.

The amount of iron that is co-administered with the levomefolate will also vary depending on the needs of the patient, but will generally range from 100 to 400 mcg/day, 150 to 300 mcg/day, or 200 mg/day, based on the weight of the iron moiety. In one embodiment, the levomefolate and iron will be administered in a unitary dosage form, and the invention provides a solid oral dosage form comprising one or more pharmaceutically acceptable excipients, from 0.333 to 1.0 mg of levomefolate or a pharmaceutically acceptable salt thereof, and from 67 to 400 mg of iron. Alternatively, the invention provides an oral dosage form comprising 333, 0.4, 0.5, or 1.0 mg of levomefolate (preferably as levomefolate calcium) and 33, 67, 100, 200, 300, or 400 mg of iron.

It is also possible, and indeed preferable, to practice any of the methods of this invention by controlling the patient's intake of folic acid. In a preferred embodiment, the methods include an additional step of precluding the administration of supplemental folic acid to said patient. The patient can be precluded from consuming pharmaceutical dosage forms that include folic acid, or precluded altogether from consuming folic acid in the patient's normal diet or supplemental dosage forms. In yet another embodiment, any of the methods can be practiced in a patient who exhibits unmetabolized folic acid in the patient's blood stream, comprising reducing the concentration of unmetabolized folic acid in said patient. In still another embodiment, any of the methods of this invention can be practiced in a population of patients consuming on average greater than 0.1 mg of folic acid per day.

A preferred salt of levomefolate is the calcium salt, although other salts can also be employed, including acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, mandelic acid, methanesulfonic acid, ethanesulfonic acid, 1,2,-ethanedisulfonic acid, 2-hydroxyethanesulfonic acid, benzenesulfonic acid p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

In addition, pharmaceutically acceptable salts may be formed when an acidic proton present is capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

Various pharmaceutical compositions can be developed that make use of the methods described herein. The compositions can be administered by any appropriate route, for example, orally, parenterally, or intravenously, in liquid or solid form.

Preferred modes of administrations of the active compounds are injectable and/or oral. These compositions will generally include an inert diluent or an edible carrier. They may be enclosed in gelatin capsules (for oral use) or compressed into tablets (for oral or buccal use) or formulated into troches (for buccal use). For these purposes, the active compound can be incorporated with excipients and used in the form of tablets, troches, or capsules. Pharmaceutically compatible binding agents, and/or adjuvant materials can be included as part of the composition.

Alternatively, the active ingredients of the present invention can be administered as part of a patient's normal diet. For example, ingestion of foods containing more than 2.4 mcg per day would constitute the administration of a therapeutically effective amount of vitamin B12 in the methods of the present invention.

Tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, or corn starch; a lubricant such as magnesium stearate; a gliding such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compounds can be administered as a component of an elixir, suspension, syrup, wafer, orally disintegrating film, orally disintegrating tablet, chewing gum or the like. A syrup may contain, in addition to the active compounds, sucrose as a sweetening agent and certain preservatives, dyes and colorings and flavors.

Solutions or suspensions used for injection can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride, mannitol and dextrose. An injectable preparation can be enclosed in ampoules, disposable syringes or multiple dose vials made of glass or plastic.

EXAMPLES

The following examples are put forth so as to provide those of ordinary skill in the art with a complete disclosure and description of how the methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for.

Example 1

Effect of Unmetabolized Folic Acid on Hemoglobin Levels

An evaluation of data gathered through NHANES was undertaken to determine the effect of unmetabolized folic acid on serum hemoglobin concentrations. NHANES monitors the nation's health and nutritional status. The survey is currently implemented as a continuous annual survey and uses a complex multistage probability design to select a representative sample of the non-institutionalized US civilian population. Consistent with NHANES analytic guidelines, this example combines data from two separate survey periods spanning 1999-2002. The methods used herein are described in greater detail in Morris et al., AM. J. CLIN. NUTR. 2012; 91:1733-44, and are repeated herein for a more thorough understanding.

A detailed description of blood collection and processing can be found in the NHANES Laboratory Procedures Manual. This particular example focuses on seniors (i.e., those aged ≥60 y), and included 3706 senior survey participants. Hemoglobin concentrations were measured at the MEC laboratory by using a MAXM hematology flow cytometer (Beckman Coulter Inc, Fullerton, Calif.). Detailed methods for all the biochemical assays can be found in the NHANES Laboratory Procedures Manuals.

Eligible participants were divided into ten deciles based on their serum folate concentrations, so that decile 1 includes the 10% of the participants having the lowest serum folate concentrations, decile 10 includes the 10% of the participants having the highest serum folate concentrations. etc. Participants in each decile were then further subdivided based on the detection of unmetabolized folic acid, and/or the participant's serum B12 or serum iron concentration, and mean hemoglobin concentrations calculated for each decile.

Data analyses were performed by using SUDAAN release 9.0 (Research Triangle Institute, Research Triangle Park, N.C.) with appropriate sampling weights, pseudo primary sampling units, and stratification variables to account for the survey's complex sampling design.

The results of the evaluation are reported below in Tables 1a, 1b, and 1c.

TABLE 1a

Relative Impact of Folic Acid and Levomefolate on Hemoglobin Concentrations

|  | Decile 1 | Decile 5 | Decile 10 |
| --- | --- | --- | --- |
| Mean Folate per decile (nmol/L) | 6.39 | 15.76 | 46.09 |
| Mean 5MeTHF per decile (nmol/L) | 7.46 | 18.45 | 38.34 |
|  | hgb conc. (g/dL) | hgb conc. (g/dL) | hgb conc. (g/dL) |
| Mean hgb per decile (g/dL) | 14.29 | 14.25 | 13.76 |
| w/ufa | 14.32 | 14.25 | 13.70 |
| w/o ufa | 14.04 | 14.28 | 14.30 |
| B12 > 200 pg/mL + ufa | 14.38 | 14.25 | 13.71 |

TABLE 1a-continued

Relative Impact of Folic Acid and Levomefolate on
Hemoglobin Concentrations

|  | Decile 1 | Decile 5 | Decile 10 |
|---|---|---|---|
| B12 > 200 pg/mL w/o ufa | 14.08 | 14.30 | 14.35 |
| iron > 60 mcg/dL + ufa | 14.62 | 14.43 | 13.93 |
| iron > 60 mcg/dL w/o ufa | 14.11 | 14.39 | 14.45 |

As can be seen, the presence of unmetabolized folic acid in survey participants uniformly decreased the mean hemoglobin concentrations as the concentration of folates in the participants' serum increased. In contrast, when unmetabolized folic acid was not detected, a rise in hemoglobin concentrations was observed along with increasing serum folate levels. These observations also held true when considering patients who exhibited normal healthy levels of vitamin B12 or iron.

Because levomefolate is the dominant species of folate in the bloodstream (>98%) in the absence of unmetabolized folic acid, these results demonstrate that levomefolate promotes healthy hematological functioning, and actually promotes the production of hemoglobin, whereas excessive folic acid reduces the production of hemoglobin.

TABLE 1b

Relative Impact of Folic Acid and Levomefolate on
Mean Corpuscular Volume

|  | decile 1 | decile 5 | decile 10 |
|---|---|---|---|
| Mean Folate per decile (nmol/L) | 6.39 | 15.76 | 46.09 |
| Mean 5MeTHF per decile (nmol/L) | 7.46 | 18.45 | 38.34 |
|  | MCV (fL) | MCV (fL) | MCV (fL) |
| Mean MCV per decile (fL) | 91.55 | 91.33 | 91.92 |
| w/supp | 91.34 | 92.16 | 92.14 |
| w/o supp | 91.62 | 90.09 | 89.51 |
| B12 > 200 pg/mL + supp | 91.09 | 92.16 | 92.47 |
| B12 > 200 pg/mL w/o supp | 91.49 | 90.13 | 89.51 |
| iron > 60 mcg/dL + supp | 92.74 | 92.87 | 92.85 |
| iron > 60 mcg/dL w/o supp | 92.41 | 90.98 | 90.71 |
| LDH > 198 U/L + supp | 90.17 | 92.23 | 93.14 |
| LDH > 198 U/L w/o supp | 89.49 | 86.46 | 85.07 |

As can be seen, MCV remained essentially the same across all ten deciles, as total folates and levomefolate concentrations increased. However, the MCV values were greatly affected by whether the survey participant was taking supplements, which predominantly contain folic acid. The use of supplements caused the MCV of survey participants to increase as the concentration of folates in the participants' serum increased. In contrast, when supplements were not used, a decrease in MCV levels was observed along with increasing serum folate levels. These observations also held true when considering patients who exhibited normal healthy levels of vitamin B12 or iron. These results indicate that while folate (particularly levomefolate) generally leads to a reduction in MCV, the administration of folic acid leads to increases in MCV.

The LDH data is also striking. As can be seen, the use of folic acid supplements in survey participants experiencing elevated LDH levels actually increased the MCV of survey participants as folate concentrations increased, whereas folate concentrations decreased MCV in survey participants who did not consume supplements:

TABLE 1c

Relative Impact of Folic Acid and Levomefolate on
Red Blood Cell Count

|  | decile 1 | decile 5 | decile 10 |
|---|---|---|---|
| Mean Folate per decile (nmol/L) | 6.39 | 15.76 | 46.09 |
| Mean 5MeTHF per decile (nmol/L) | 7.46 | 18.45 | 38.34 |
|  | RCC (million/uL blood) | RCC (million/uL blood) | RCC (million/uL blood) |
| Mean RCC per decile (million/uL blood) | 4.64 | 4.61 | 4.43 |
| w/supp | 4.47 | 4.58 | 4.41 |
| w/o supp | 4.71 | 4.67 | 4.60 |

As can be seen, for each of the deciles reported, survey participants who did not consume folic acid supplements had a much higher red cell count than survey participants who consumed folic acid supplements, even though the survey participants had the same folate levels. Once again, this demonstrates that red cell count is improved in the absence of folic acid.

Example 2

Impact of Folic Acid Supplements on Mean
Corpuscular Volume

In order to determine whether folic acid supplements could be affecting the incidence of macrocytosis in the United States or whether folic acid supplements could be negatively influencing macrocytic processes, NHANES data reported in Ganji et al., AM. J. CLIN. NUTR. 2009; 89:363-71, were reanalyzed, this time over an extended time period from 1988-1994 until 1999-2004, to determine the impact of supplement use on the incidence of macrocytosis and mean corpuscular volume. Unless otherwise indicated, NHANES data collection methods were substantially the same as in Examples 1 and 2.

This study used data from 4 surveys: NHANES 1988-1994, NHANES 1999-2000, NHANES 2001-2002, and NHANES 2003-2004. For the purpose of comparing data in the latter time period, NHANES 1999-2000, NHANES 2001-2002, and NHANES 2003-2004 data were concatenated into one analytic data set, NHANES 1999-2004, according to the NHANES guidelines. SEMs and percentages were estimated with the Taylor Series Linearization method. After applying standard exclusion criteria, the final study sample consisted of 26,596 individuals (men ¼ 12,671; women ¼ 13,926).

For NHANES 1988-1994 and 1999-2004, multivariate-adjusted and univariate values for hemoglobin, hematocrit, and MCV and prevalence rates (%) for overall anemia and macrocytosis were determined according to sex, race-ethnicity, age, poverty, and vitamin/mineral supplement use (yes or no). Prevalence of anemia (%) based on low hemoglobin concentrations and prevalence of macrocytosis (%) based on high MCV values were determined for the aforementioned demographic categories. The differences in hemoglobin, hematocrit, MCV, and prevalence of anemia and macrocytosis between NHANES 1988-1994 and NHANES 1999-2004 were determined with a 2-tailed unpaired t test.

The likelihood of having anemia and macrocytosis between the two time periods studied was determined with logistic regression after the adjustment for race-ethnicity, age, poverty:income ratio, and vitamin/supplement use in men and women. Additionally, for both sexes, the likelihood of vitamin/mineral supplement use in the period after folic acid fortification began relative to that before folic acid fortification began was determined with logistic regression after adjustment for sex, race-ethnicity, age, and poverty: income ratio. In all analyses, a P<0.05 was considered significant.

The results of the study, for men only, are reported below in Table 2.

TABLE 2

Impact of Folic Acid Supplements on Anemia and Macrocytosis

|  | 1988-1994 | 1999-2004 |
| --- | --- | --- |
| Study Participants (n) | 6334 | 6037 |
| Folate Intake | 291.5 mcg DFE[3] | 291.5 mcg DFE + 111 mcg FA[4] |
| Folic Acid Supplement Use | 32% | 43% |
| Yes | 2140 | 2600 |
| No | 4494 | 3437 |
| Hemoglobin (g/dL) | 15.1 ± 0.04 | 15.4 ± 0.04 |
| MCV (fL) | 90.2 ± 0.2 | 90.7 ± 0.1 |
| Anemia Prevalence[1] | 3.3 ± 0.3 | 2.9 ± 0.2 |
| Macrocytosis Prevalence[2] | 4.0 ± 0.4 | 4.3 ± 0.3 |
| Anemia Cases | 428 | 296 |
| Macrocytosis Cases | 319 | 323 |

[1]Anemia was defined as a hemoglobin concentration <12 g/dL (women) or <13 g/dL (men).
[2]Macrocytosis was defined as Mean cell volume ≥99 fL.
[3]Daily Folate Equivalents
[4]Folic Acid As can be seen, the prevalence of anemia dropped during the study period with the increased use of folic acid supplements. However, the incidence of macrocytosis increased during the study period, and was associated with an increase in the mean corpuscular volume of study participants.

Example 3

Differences in Responses to Folate Depending on Vitamin B12 Status

Data collected in the National Health and Nutrition Examination Survey ("NHANES") conducted during years 1999-2002, as reported in Selhub et al., AM J. CLIN. NUTR. 2009:89 (suppl):702S-6S, were also used to compare the effect of serum folate levels on homocysteine and methylmalonic acid in vitamin B12 deficient and vitamin B12 normal patients. Low vitamin B-12 status was defined as serum vitamin B-12<148 pmol/L or serum MMA >210 nmol/L, which are above the published reference range for serum vitamin B-12-replete survey participants with normal serum creatinine concentrations in Pfeiffer et al., Am J. Clin. Nutr. 2005; 82:442-50.

Briefly, 3706 senior survey participants (i.e., those aged ≥60 y) were evaluated. Of the 1684 subjects who met eligibility requirements, complete data for analyses pertaining to anemia were available for 1458 subjects. Blood samples were drawn and analyzed for biochemical markers, and a complete blood count was performed, according to NHANES defined protocols. Values were generated with the use of SUDAN PROC REGRESS after controlling for age, race-ethnicity, sex, cigarette smoking, alcohol intake, BMI, self-reported diabetes status, and serum concentrations of creatinine and alanine aminotransferase. The results for MMA and HCY in a vitamin B12 deficient population, defined as having a serum B12 concentration less than 148 pmol/L, are presented below in Table 3a.

TABLE 3a

Effect of serum folate concentrations on serum HCY concentrations and serum MMA concentrations (geometric mean) in a vitamin B12 deficient population.

| Serum Folate (nmol/L)* | Serum HCY (umol/L) | Serum MMA (nmol/L) |
| --- | --- | --- |
| 16 | 9.9 | 174 |
| 23 | 10.8 | 265 |
| 30 | 10.5 | 265 |
| 44 | 11.8 | 314 |

*Values in this column are category medians

As can be seen, homocysteine and methylmalonic acid concentrations both increased with increasing folate status among people with low serum concentrations of vitamin B-12. These analyses were also run in a cohort of patients replete in vitamin B12 (defined as having a serum B12 concentration greater than or equal to 148 pmol/L). Once again, values were generated with the use of SUDAN PROC REGRESS after controlling for age, race-ethnicity, sex, cigarette smoking, alcohol intake, BMI, self-reported diabetes status, and serum concentrations of creatinine and alanine aminotransferase. The results are reported below in Table 3b.

TABLE 3b

Effect of serum folate concentrations on serum HCY and serum MMA concentrations (geometric means) in a vitamin B12 replete population from NHANES 1999-2002.

| Serum Folate (nmol/L)* | Serum HCY (umol/L) | Serum MMA (nmol/L) |
| --- | --- | --- |
| 16 | 9.2 | 138 |
| 23 | 8.0 | 137 |
| 30 | 7.5 | 132 |
| 44 | 7.1 | 128 |

*Values in this column are category medians

As can be seen from Table 3b, increases in folate concentrations in a vitamin B12 replete population have the opposite effect than increases in folate concentrations in a vitamin B12 deficient population. Whereas increasing folate concentrations results in an increase in MMA and HCY concentrations in a vitamin B12 deficient population, increasing folate concentrations results in a decrease in MMA and HCY if the population is replete in vitamin B12.

These results demonstrate the importance of administering adequate vitamin B12 during folate supplementation, to ensure that folate supplementation has its intended effect on markers of hematological health.

Example 4

Effect of Varying Concentrations of Vitamin B12 or Folate Species on Deoxyuridine Suppression Test in Megaloblastic Bone Marrow Cells Deoxyuridine ("dU") suppression data described in Taheri et al., Blood, Vol. 59, No. 3 (March 1982) were re-analyzed to compare the effect of various folate analogs on megaloblastic processes. In this test the DNA of bone marrow cells is labeled with (3H)-thymidine (3H-TdR) via the salvage pathway (see MacAllan et al. (Proc. Natl. Acad. Sci. USA 95 (1998)). In a second incubation, nonradioactive dU at high concentration is added. This inhibits (3H)-TdR uptake due at least in part to competition by thymidine nucleotides synthesized de novo from the cold dU. The dU suppression test is expressed as a percentage of the (3H)-TdR incorporation in the absence of dU. Megaloblastic marrow cells give higher values than normal due to the impaired conversion of dU to thymidine nucleotides. Addition of vitamin B12 or folate analogues to megaloblastic marrow restores dU suppression to normal values in a manner specific for the appropriate vitamin deficiency. In this example, the folate analogues tested were folinic acid, tetrahydrofolate, folic acid, and levomefolate.

Bone marrow samples were obtained by aspiration from the posterior iliac crest of 25 patients with confirmed megaloblastic anemia and 14 normal volunteers. Patients were classified as being B12 deficient, folate deficient, or both on the basis of serum levels of these vitamins. Normal ranges used in the study were: serum vitamin B12, 160-925 ng/L (*E gracilis* assay) and serum folate, 3-20/1 (*L. casei* assay). The results of the testing are presented in Table 4. dU suppression test values are expressed as (3H)-TdR incorporated into DNA in the presence of dU as a percentage of (3H)-TdR incorporation in the absence of dU.

TABLE 4

Effect of Varying Concentrations of Vitamin B12 or Folate Species on the dU Suppression Test in Megaloblastic Bone Marrow Cells

|  |  | B12 Deficiency | Folate Deficiency |
|---|---|---|---|
| +dU (1 um alone) |  | 14.9 | 17.2 |
| +dU + B12 | 100 mcg/ml | 5.7 | 16.3 |
|  | 10 mcg/ml | 5.8 | 12.3 |
| +dU + folinic acid | 30 | 1.6 | 1.0 |
|  | 15 | 2.2 | — |
|  | 6 | 2.0 | 1.3 |
|  | 3 | 1.9 | 1.9 |
|  | 1 | 2.5 | 1.9 |
|  | 0.3 | 4.5 | 3.4 |
| +dU + THF | 300 | 2.4 | 1.9 |
|  | 75 | 3.5 | — |
|  | 30 | 5.0 | 2.2 |
|  | 15 | 4.9 | 2.1 |
|  | 6 | 6.3 | 2.5 |
|  | 3 | 9.3 | 4.0 |
|  | 1 | 8.1 | 8.6 |
|  | 0.3 | 10.8 | 14.3 |
| +dU + folic acid | 50 | 4.1 | 2.3 |
|  | 5 | — | 5.5 |
|  | 3 | 12 | — |
|  | 1 | 14.8 | 10.3 |
| +dU + me-THF | 300 | 15.7 | 4.3 |
|  | 75 | 18.4 | — |
|  | 30 | 12.9 | 4.5 |
|  | 15 | — | 2.7 |
|  | 6 | — | 4.6 |
|  | 3 | 16.1 | 3.9 |
|  | 1 | — | — |

In all types of vitamin deficiency, folinic acid was most effective in overcoming the defect in DNA precursor synthesis. In megaloblastic anemia due to vitamin B12 deficiency, folinic acid gave excellent correction at levels as low as 0.3 mL/ml, while tetrahydrofolate (THF) only gave correction above 6 mL/ml. In contrast, levomefolate (LMF) did not restore normal dU suppression in vitamin B12 deficiency even at 300 mcg/ml. Thus, levomefolate does not have the same potential for masking a vitamin B12 deficiency as the other folate species.

Example 5

Oral Formulations

Formulations of representative oral tablets comprising 1.0 mg of levomefolate as its calcium salt is presented below in Tables 5a-5c.

TABLE 5a

Representative Tablet Formulation

| Ingredient | Weight |
|---|---|
| Levomefolate Calcium* | 1.0 mg |
| Cyanocobalamin | 1.0 mg |
| Microcrystalline Cellulose | 73.0 mg |
| Stearic Acid | 25.0 mg |
| Colloidal Silica | 1.5 mg. |

*Based on weight of calcium salt.

TABLE 5b

Representative Tablet Formulation

| Ingredient | Weight |
|---|---|
| Levomefolate Calcium* | 1.0 mg |
| Cyanocobalamin | 0.025 mg |
| Microcrystalline Cellulose | 73.0 mg |
| Stearic Acid | 25.0 mg |
| Colloidal Silica | 1.5 mg. |

*Based on weight of calcium salt.

TABLE 5c

Representative Tablet Formulation

| Ingredient | Weight |
|---|---|
| Levomefolate Calcium* | 333 mg |
| Ferrous Sulfate** | 67 mg |
| Microcrystalline Cellulose | 73.0 mg |
| Stearic Acid | 25.0 mg |
| Colloidal Silica | 1.5 mg. |

*Based on weight of calcium salt.
**Based on weight of iron moiety.

Throughout this application, various publications are referenced. The disclosures of these publications are hereby incorporated by reference in order to more fully describe the state of the art to which this invention pertains. It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A method of treating impaired folate metabolism due to anti-folate therapy comprising administering to said subject a therapeutically effective amount of levomefolate or a pharmaceutically acceptable salt thereof, optionally in combination with a second therapeutic agent selected from vitamin B12 and iron, further comprising administering to said subject an anti-folate drug selected from methotrexate and pemetrexed.

2. The method of claim 1 further comprising administering to said subject a therapeutically effective amount of vitamin B12.

3. A method of modulating a hematological marker in a human subject in need thereof comprising administering to said subject a therapeutically effective amount of levomefolate or a pharmaceutically acceptable salt thereof, optionally in combination with a second therapeutic agent selected from vitamin B12 and iron, wherein said method of modulating a hematological marker comprises: (a) increasing serum hemoglobin levels; (b) lowering serum lactate dehydrogenase levels; (c) lowering serum C-reactive protein levels; (d) lowering mean corpuscular volume levels; (e) increasing red cell count levels; (f) lowering serum homocysteine levels; (g) lowering serum methylmalonic acid levels; and (h) increasing reticulocyte levels.

4. The method of claim 3 further comprising administering to said subject a therapeutically effective amount of vitamin B12.

5. The method of claim 3 further comprising administering to said subject a therapeutically effective amount of iron.

6. The method of claim 3 wherein said subject has an MCV greater than 100 fL and a serum folate level less than 3 ng/mL.

7. The method of claim 3 wherein said subject has an MCV greater than 100 fL, a serum folate level less than 3 ng/mL, a serum vitamin B12 level greater than 200 pg/mL, a serum LDH concentration greater than 198 IU/L, and a serum HCY concentration greater than 16 umol/L.

8. The method of claim 3 wherein said subject has an MCV greater than 100 fL, a serum folate level less than 3 ng/mL, blood cell morphology characterized by hypersegmented neutrophils, and bone megaloblastic marrow pathology.

9. The method of claim 3 wherein said subject has an MCV greater than 100 fL, a serum folate level less than 3 ng/mL, a serum vitamin B12 level greater than 200 pg/mL, a serum LDH concentration greater than 198 IU/L, a serum HCY concentration greater than 16 umol/L, blood cell morphology characterized by hypersegmented neutrophils, and megaloblastic bone marrow pathology.

10. The method of claim 3, wherein said method reduces the concentration of unmetabolized folic acid in said subject.

11. A method of modulating a hematological marker in a human subject in need thereof comprising administering to said subject a therapeutically effective amount of levomefolate or a pharmaceutically acceptable salt thereof, optionally in combination with a second therapeutic agent selected from vitamin B12 and iron, wherein said method of modulating a hematological marker comprises: (a) increasing serum hemoglobin levels; (b) lowering serum lactate dehydrogenase levels; (c) lowering mean corpuscular volume levels; (d) increasing red cell count levels; (e) lowering serum homocysteine levels; and (f) increasing reticulocyte levels.

12. The method of claim 11 further comprising administering to said subject a therapeutically effective amount of vitamin B12.

13. The method of claim 11 further comprising administering to said subject a therapeutically effective amount of iron.

14. The method of claim 11 further comprising administering to said subject an anti-folate drug selected from methotrexate, pemetrexed, proquanil, pyrimethamine, trimethoprim, trimetrexate, edatrexate, piritrexim, and lometrexol.

15. The method of claim 11 wherein said subject has an MCV greater than 100 fL and a serum folate level less than 3 ng/mL.

16. The method of claim 11 wherein said subject has an MCV greater than 100 fL, a serum folate level less than 3 ng/mL, a serum vitamin B12 level greater than 200 pg/mL, a serum LDH concentration greater than 198 IU/L, and a serum HCY concentration greater than 16 umol/L.

17. The method of claim 11 wherein said subject has an MCV greater than 100 fL, a serum folate level less than 3 ng/mL, blood cell morphology characterized by hypersegmented neutrophils, and bone megaloblastic marrow pathology.

18. The method of claim 11 wherein said subject has an MCV greater than 100 fL, a serum folate level less than 3 ng/mL, a serum vitamin B12 level greater than 200 pg/mL, a serum LDH concentration greater than 198 IU/L, a serum HCY concentration greater than 16 umol/L, blood cell morphology characterized by hypersegmented neutrophils, and megaloblastic bone marrow pathology.

19. The method of claim 11, wherein said method reduces the concentration of unmetabolized folic acid in said subject.

* * * * *